(12) United States Patent
Ducharme et al.

(10) Patent No.: US 8,361,054 B2
(45) Date of Patent: Jan. 29, 2013

(54) APPARATUS AND METHODS FOR CONTAINING AND DELIVERING THERAPEUTIC AGENTS

(75) Inventors: Richard W. Ducharme, Winston-Salem, NC (US); David E. Sugg, Cornelius, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 444 days.

(21) Appl. No.: 12/633,027

(22) Filed: Dec. 8, 2009

(65) Prior Publication Data
US 2010/0160897 A1  Jun. 24, 2010

Related U.S. Application Data

(60) Provisional application No. 61/140,379, filed on Dec. 23, 2008.

(51) Int. Cl.
*A61M 5/168* (2006.01)
(52) U.S. Cl. ............. 604/508; 604/118; 604/82; 604/85
(58) Field of Classification Search ............. 604/58, 604/82, 508, 118, 70, 24, 83, 85
See application file for complete search history.

(56) References Cited

U.S. PATENT DOCUMENTS

| 39,678 A | 8/1863 | Russell |
|---|---|---|
| 170,182 A | 11/1875 | Molesworth |
| 442,785 A | 12/1890 | Schoettl |
| 460,458 A | 9/1891 | Bates |
| 471,865 A | 3/1892 | Howard |
| 533,489 A | 2/1895 | Ogram |
| 566,411 A | 8/1896 | Schoene |
| 576,437 A | 2/1897 | Elliott |
| 693,587 A | 2/1902 | Campbell |
| 775,985 A | 11/1904 | McKain |
| 881,238 A | 3/1908 | Hasbrouck |
| 904,149 A | 11/1908 | Rachmann |

(Continued)

FOREIGN PATENT DOCUMENTS

| CH | 15244 A | 9/1897 |
|---|---|---|
| CH | 257250 A | 9/1948 |

(Continued)

OTHER PUBLICATIONS

International Search Report and Written Opinion for PCT/US2010/036381, mailed Aug. 20, 2010, 16 pgs.

(Continued)

*Primary Examiner* — Kevin C Sirmons
*Assistant Examiner* — Michael J Anderson
(74) *Attorney, Agent, or Firm* — Brinks Hofer Gilson & Lione

(57) ABSTRACT

The present embodiments provide apparatus and methods suitable for containing and delivering a therapeutic agent to a target site. The apparatus generally comprises at least one container for holding a therapeutic agent, and a pressure source for facilitating delivery of the therapeutic agent. In one embodiment, the pressure source may be placed in selective fluid communication with a proximal region of the container and fluid from the pressure source may flow through at least a portion of the container to urge the therapeutic agent through the container towards the target site. In an alternative embodiment, the pressure source may be selectively in fluid communication with either a first hollow tube and the container so that therapeutic agent is urged into a catheter, or with a second hollow tube and a catheter so that a fluid from the pressure source bypasses the container and enters the catheter.

10 Claims, 7 Drawing Sheets

U.S. PATENT DOCUMENTS

| | | | |
|---|---|---|---|
| 938,648 A | 11/1909 | DeVilbiss | |
| 1,022,601 A | 4/1912 | Rumberg et al. | |
| 1,114,114 A | 10/1914 | Cochenour | |
| 1,145,520 A | 7/1915 | Smith | |
| 1,261,503 A | 4/1918 | Figgis | |
| 1,357,452 A | 11/1920 | Hall | |
| 1,466,119 A | 8/1923 | Claflin | |
| 1,521,396 A | 12/1924 | Scott | |
| 1,685,280 A | 9/1928 | Findley | |
| 1,934,793 A | 11/1933 | Crain et al. | 128/266 |
| 2,004,402 A | 6/1935 | Conklin | 128/173 |
| 2,151,418 A | 3/1939 | Bolte | 128/265 |
| 2,223,611 A | 12/1940 | Gross | 128/266 |
| 2,307,986 A | 1/1943 | Bolte et al. | 128/266 |
| 2,390,313 A | 12/1945 | Macgill | 299/86 |
| 2,507,702 A | 5/1950 | Fields | 128/266 |
| 2,519,555 A | 8/1950 | Fields | 128/266 |
| 2,609,155 A | 9/1952 | Fosnaugh | |
| 2,632,444 A | 3/1953 | Kas | 128/217 |
| 2,850,013 A | 9/1958 | Cordis | 128/217 |
| 2,934,314 A | 4/1960 | Chambers et al. | 251/331 |
| 2,956,579 A | 10/1960 | Moore et al. | 137/218 |
| 3,016,895 A | 1/1962 | Sein et al. | 128/217 |
| 3,050,261 A | 8/1962 | Littlefield | 239/318 |
| 3,506,008 A | 4/1970 | Huck | 128/261 |
| 3,540,444 A | 11/1970 | Moreland | 128/173 |
| 3,572,335 A | 3/1971 | Robinson | 128/217 |
| 3,589,363 A | 6/1971 | Banko et al. | 128/276 |
| 3,599,866 A | 8/1971 | Bolton | 239/8 |
| 3,632,046 A | 1/1972 | Hengesbach | 239/318 |
| 3,647,143 A | 3/1972 | Gauthier et al. | 239/342 |
| 3,649,299 A | 3/1972 | Sholl | 99/107 |
| 3,667,465 A | 6/1972 | Voss | 128/271 |
| 3,710,400 A | 1/1973 | Sparks | |
| 3,742,955 A | 7/1973 | Battista et al. | 128/334 |
| 3,744,493 A | 7/1973 | Booher et al. | 128/217 |
| 3,762,410 A | 10/1973 | Bindel | 128/229 |
| 3,788,315 A | 1/1974 | Laurens | 128/173 H |
| 3,815,595 A | 6/1974 | Bar | 128/184 |
| 3,900,022 A | 8/1975 | Widran | |
| 3,916,896 A | 11/1975 | Ballard | 128/239 |
| 4,017,007 A | 4/1977 | Riccio | 222/80 |
| 4,040,420 A | 8/1977 | Speer | 128/218 |
| 4,174,811 A | 11/1979 | Binder et al. | 239/308 |
| 4,184,258 A | 1/1980 | Barrington et al. | 433/88 |
| 4,204,539 A | 5/1980 | Van Brugge | 128/223 |
| 4,204,645 A | 5/1980 | Hopp | 239/341 |
| 4,210,140 A | 7/1980 | James et al. | 128/266 |
| 4,359,049 A | 11/1982 | Redl et al. | 128/218 |
| 4,423,727 A | 1/1984 | Widran et al. | |
| 4,427,650 A | 1/1984 | Stroetmann | 424/46 |
| 4,516,442 A | 5/1985 | Davis | 74/529 |
| 4,534,345 A | 8/1985 | Wetterlin | 128/203.15 |
| 4,539,716 A | 9/1985 | Bell | |
| 4,552,556 A * | 11/1985 | Urquhart et al. | 604/80 |
| 4,578,067 A | 3/1986 | Cruz, Jr. | 604/368 |
| 4,606,501 A | 8/1986 | Bate et al. | 239/346 |
| 4,620,847 A | 11/1986 | Shishov et al. | 604/58 |
| 4,631,055 A | 12/1986 | Redl et al. | 604/82 |
| 4,637,816 A | 1/1987 | Mann | 604/62 |
| H257 H | 4/1987 | Barditch et al. | |
| 4,655,211 A | 4/1987 | Sakamoto et al. | 128/156 |
| 4,735,616 A | 4/1988 | Eibl et al. | 604/191 |
| 4,738,658 A | 4/1988 | Magro et al. | 604/53 |
| 4,738,740 A | 4/1988 | Pinchuk | |
| 4,752,466 A | 6/1988 | Saferstein et al. | 424/46 |
| 4,790,819 A | 12/1988 | Li et al. | 604/59 |
| 4,798,606 A | 1/1989 | Pinchuk | |
| 4,803,977 A | 2/1989 | Kremer, Jr. | 600/3 |
| 4,846,405 A | 7/1989 | Zimmermann | 239/422 |
| D303,139 S | 8/1989 | Morgan | D23/223 |
| 4,872,450 A | 10/1989 | Austad | 128/90 |
| 4,874,368 A | 10/1989 | Miller et al. | 604/82 |
| 4,890,612 A | 1/1990 | Kensey | 606/213 |
| 4,900,303 A | 2/1990 | Lemelson | 604/54 |
| 4,902,278 A | 2/1990 | Maget et al. | |
| 4,902,281 A | 2/1990 | Avoy | 604/191 |
| 4,927,410 A | 5/1990 | Kovacs | |
| 4,929,246 A | 5/1990 | Sinofsky | 606/8 |
| 4,941,874 A | 7/1990 | Sandow et al. | 604/60 |
| 4,941,880 A | 7/1990 | Burns | 604/143 |
| 4,945,050 A | 7/1990 | Sanford et al. | 435/172.1 |
| 4,946,870 A | 8/1990 | Partain, III. et al. | 514/777 |
| 4,950,234 A | 8/1990 | Fujioka et al. | 604/60 |
| 4,969,874 A | 11/1990 | Michel et al. | |
| 4,978,336 A | 12/1990 | Capozzi et al. | 604/82 |
| 4,994,028 A | 2/1991 | Leonard et al. | 604/60 |
| 5,009,637 A | 4/1991 | Newman et al. | 604/68 |
| 5,015,580 A | 5/1991 | Christou et al. | 435/172.3 |
| 5,021,059 A | 6/1991 | Kensey et al. | 606/213 |
| 5,053,000 A | 10/1991 | Booth et al. | 604/20 |
| 5,059,187 A | 10/1991 | Sperry et al. | 604/290 |
| 5,061,180 A | 10/1991 | Wiele | 433/91 |
| 5,063,025 A | 11/1991 | Ito | 422/100 |
| 5,064,413 A * | 11/1991 | McKinnon et al. | 604/70 |
| 5,106,370 A | 4/1992 | Stewart | 604/61 |
| 5,116,315 A | 5/1992 | Capozzi et al. | 604/82 |
| 5,120,657 A | 6/1992 | McCabe et al. | 435/287 |
| 5,129,825 A | 7/1992 | Discko, Jr. | 433/90 |
| 5,129,882 A | 7/1992 | Weldon et al. | 604/96 |
| 5,133,701 A | 7/1992 | Han | 604/289 |
| 5,141,515 A | 8/1992 | Eberbach | 606/151 |
| 5,147,292 A | 9/1992 | Kullas et al. | 604/34 |
| 5,149,655 A | 9/1992 | McCabe et al. | 435/287 |
| 5,165,604 A | 11/1992 | Copp, Jr. | 239/106 |
| 5,176,642 A | 1/1993 | Clement | |
| 5,179,022 A | 1/1993 | Sanford et al. | 435/287 |
| D333,000 S | 2/1993 | Good et al. | D24/108 |
| 5,204,253 A | 4/1993 | Sanford et al. | 435/172.3 |
| 5,219,328 A | 6/1993 | Morse et al. | 604/49 |
| 5,226,567 A | 7/1993 | Sansalone | 222/195 |
| 5,226,877 A | 7/1993 | Epstein | 604/35 |
| RE34,365 E * | 8/1993 | Theeuwes | 604/85 |
| 5,273,531 A | 12/1993 | Knoepfler | 604/58 |
| 5,292,309 A | 3/1994 | Van Tassel et al. | 604/117 |
| 5,310,407 A | 5/1994 | Casale | |
| 5,312,333 A | 5/1994 | Churinetz et al. | 604/57 |
| 5,328,459 A | 7/1994 | Laghi | 604/35 |
| 5,330,426 A * | 7/1994 | Kriesel et al. | 604/89 |
| 5,391,183 A | 2/1995 | Janzen et al. | 606/213 |
| 5,392,992 A | 2/1995 | Farnsteiner et al. | 239/296 |
| 5,395,326 A | 3/1995 | Haber et al. | 604/90 |
| 5,405,607 A | 4/1995 | Epstein | 424/94.64 |
| 5,415,631 A | 5/1995 | Churinetz et al. | 604/57 |
| 5,429,278 A | 7/1995 | Sansalone | 222/195 |
| 5,445,612 A | 8/1995 | Terakura et al. | 604/58 |
| 5,447,499 A | 9/1995 | Allaire et al. | 602/42 |
| 5,469,994 A | 11/1995 | Reh et al. | 222/630 |
| 5,470,311 A | 11/1995 | Setterstrom et al. | 604/24 |
| 5,484,403 A | 1/1996 | Yoakum et al. | 604/59 |
| 5,503,623 A | 4/1996 | Tilton, Jr. | |
| 5,520,658 A | 5/1996 | Holm | 604/191 |
| 5,538,162 A | 7/1996 | Reh et al. | 222/63 |
| 5,553,741 A | 9/1996 | Sancoff et al. | 222/1 |
| 5,558,646 A | 9/1996 | Roche | 604/143 |
| 5,582,596 A | 12/1996 | Fukunaga et al. | 604/191 |
| 5,584,807 A | 12/1996 | McCabe | 604/71 |
| 5,584,815 A | 12/1996 | Pawelka et al. | 604/191 |
| 5,601,603 A | 2/1997 | Illi | 606/213 |
| 5,605,541 A | 2/1997 | Holm | 604/82 |
| 5,612,050 A | 3/1997 | Rowe et al. | 424/423 |
| 5,665,067 A | 9/1997 | Linder et al. | |
| 5,697,947 A | 12/1997 | Wolf et al. | 606/185 |
| 5,707,402 A | 1/1998 | Heim | 607/88 |
| 5,749,968 A | 5/1998 | Melanson et al. | 118/300 |
| 5,759,171 A | 6/1998 | Coelho et al. | 604/82 |
| 5,788,625 A | 8/1998 | Plouhar et al. | |
| 5,865,796 A * | 2/1999 | McCabe | 604/71 |
| 5,873,530 A | 2/1999 | Chizinsky | |
| 5,902,228 A | 5/1999 | Schulsinger et al. | |
| 5,919,184 A | 7/1999 | Tilton, Jr. | |
| 5,951,531 A * | 9/1999 | Ferdman et al. | 604/290 |
| 6,007,515 A | 12/1999 | Epstein et al. | |
| 6,013,050 A | 1/2000 | Bellhouse et al. | 604/70 |
| 6,021,776 A | 2/2000 | Allred et al. | |
| 6,027,471 A | 2/2000 | Fallon et al. | 604/59 |
| 6,059,749 A | 5/2000 | Marx | |

| | | | |
|---|---|---|---|
| 6,077,217 A | 6/2000 | Love et al. | |
| 6,117,150 A | 9/2000 | Pingleton et al. | 606/167 |
| 6,165,201 A | 12/2000 | Sawhney et al. | 606/214 |
| 6,368,300 B1 | 4/2002 | Fallon et al. | |
| 6,394,975 B1 | 5/2002 | Epstein | 604/43 |
| 6,428,505 B1* | 8/2002 | Taylor | 604/80 |
| 6,454,786 B1 | 9/2002 | Holm et al. | 606/214 |
| 6,461,325 B1 | 10/2002 | Delmotte et al. | 604/82 |
| 6,461,361 B1 | 10/2002 | Epstein | 606/82 |
| 6,478,754 B1 | 11/2002 | Babaev | 601/2 |
| 6,537,246 B1* | 3/2003 | Unger et al. | 604/82 |
| 6,554,792 B2* | 4/2003 | Hughes | 604/85 |
| 6,610,026 B2 | 8/2003 | Cragg et al. | |
| 6,641,800 B1 | 11/2003 | Mistry et al. | 424/46 |
| 6,689,108 B2 | 2/2004 | Lavi et al. | 604/211 |
| 6,716,190 B1 | 4/2004 | Glines et al. | 604/70 |
| 6,723,067 B2 | 4/2004 | Nielson | |
| 6,811,550 B2 | 11/2004 | Holland et al. | |
| 6,843,388 B1 | 1/2005 | Hollars | 222/5 |
| 6,863,660 B2 | 3/2005 | Marx | |
| 6,905,475 B2* | 6/2005 | Hauschild et al. | 604/70 |
| 6,939,324 B2 | 9/2005 | Gonnelli et al. | 604/142 |
| 7,101,862 B2 | 9/2006 | Cochrum et al. | |
| 7,156,880 B2 | 1/2007 | Evans et al. | |
| 7,182,748 B1* | 2/2007 | Potter et al. | 604/70 |
| 7,291,133 B1 | 11/2007 | Kindler et al. | 604/247 |
| 7,334,598 B1 | 2/2008 | Hollars | 137/116.3 |
| 7,534,449 B2 | 5/2009 | Saltzman et al. | 427/417 |
| 7,544,177 B2 | 6/2009 | Gertner | 604/24 |
| 7,632,245 B1 | 12/2009 | Cowan et al. | 604/131 |
| 7,673,783 B2 | 3/2010 | Morgan et al. | |
| 7,691,244 B2 | 4/2010 | Levitan et al. | 204/450 |
| 7,744,526 B2 | 6/2010 | McAllister et al. | 600/36 |
| 7,776,822 B2 | 8/2010 | Terman | 514/12 |
| 7,824,373 B2 | 11/2010 | Kim | 604/141 |
| 7,857,167 B1 | 12/2010 | Hollars | 222/5 |
| 2001/0056256 A1* | 12/2001 | Hughes et al. | 604/85 |
| 2002/0165483 A1* | 11/2002 | Miller et al. | 604/82 |
| 2002/0169416 A1 | 11/2002 | Gonnelli | |
| 2003/0023202 A1* | 1/2003 | Nielson | 604/80 |
| 2003/0108511 A1 | 6/2003 | Sawhney | 424/78.08 |
| 2003/0170250 A1 | 9/2003 | Ezrin et al. | |
| 2003/0181917 A1* | 9/2003 | Gertner | 606/82 |
| 2003/0216695 A1 | 11/2003 | Yang | |
| 2004/0059283 A1* | 3/2004 | Kirwan et al. | 604/23 |
| 2005/0070848 A1 | 3/2005 | Kim et al. | 604/140 |
| 2006/0002852 A1 | 1/2006 | Saltzman et al. | |
| 2006/0052295 A1 | 3/2006 | Terman | |
| 2006/0286664 A1 | 12/2006 | McAllister et al. | |
| 2007/0088317 A1* | 4/2007 | Hyde | 604/500 |
| 2007/0240989 A1 | 10/2007 | Levitan et al. | |
| 2007/0241119 A1 | 10/2007 | Durkin et al. | 221/2 |
| 2008/0027272 A1 | 1/2008 | Kadykowski | |
| 2008/0132891 A1 | 6/2008 | Nobis et al. | |
| 2008/0287911 A1* | 11/2008 | El-Nounou et al. | 604/508 |
| 2009/0234374 A1 | 9/2009 | Gabel et al. | |
| 2009/0234380 A1 | 9/2009 | Gabel et al. | |
| 2009/0248056 A1 | 10/2009 | Gabel et al. | |
| 2010/0137796 A1 | 6/2010 | Perry et al. | 604/98.01 |

FOREIGN PATENT DOCUMENTS

| | | |
|---|---|---|
| DE | 3024749 A1 | 2/1982 |
| DE | 3108918 A1 | 9/1982 |
| DE | 3613762 A1 | 11/1987 |
| EP | 0 308 269 A1 | 9/1988 |
| EP | 0 738 498 A1 | 4/1996 |
| GB | 10563 A | 0/1896 |
| GB | 1 254 534 A | 11/1971 |
| JP | 4-22109 B | 4/1992 |
| SU | 978999 | 12/1982 |
| WO | WO 82/03545 | 10/1982 |
| WO | WO 85/02346 A1 | 6/1985 |
| WO | WO 92/20312 | 11/1992 |
| WO | WO 94/28798 | 12/1994 |
| WO | WO 96/25190 | 8/1996 |
| WO | WO 96/37245 | 11/1996 |
| WO | WO 96/40327 | 12/1996 |
| WO | WO 97/20585 A1 | 6/1997 |
| WO | WO 02/053014 A2 | 7/2002 |
| WO | WO 2004/073863 A2 | 9/2004 |
| WO | WO 2005/100980 A2 | 10/2005 |
| WO | WO 2008/008845 A2 | 1/2008 |

OTHER PUBLICATIONS

International Preliminary Report on Patentability for PCT/US2009/042781, mailed Nov. 18, 2010, 11 pgs.

International Search Report completed Sep. 22, 2009 for PCT/US2009/042781, 7 pgs.

Alto Shooter Catalog, Kaigen, English and Japanese, Jun. 1994, 8 pgs.

Decker, "An Efficient Method for The Application of Avitene® Hemostatic Agent", Surgery, Gynecology & Obstetrics, 1991, vol. 172, No. 6, 2 pgs.

Endo-Avitene™ brochure, Med Chem Products, Inc., date unknown, 4 pgs.

Fagelman, et al., "A Simple Method for Application of Microfibrillar Collagen," Surgery, Gynecology & Obstetrics, Jun. 1980, vol. 150, No. 6, 3 pgs.

Hoshino et al., "Trans-endoscopic Drug Propulsion Therapy", Digestive Endoscopy, 1993 vol. 5, 6 pgs.

The Surgical Armamentarium, Copyright 1973, V. Mueller, 3 pgs.

Response to Office Action dated Nov. 3, 2010 for U.S. Appl. No. 12/435,574, 10 pgs.

Final Office Action dated Feb. 17, 2011 for U.S. Appl. No. 12/435,574, 8 pgs.

Non-Final Office Action dated Apr. 14, 2011 for U.S. Appl. No. 12/787,796, 9 pgs.

Office Action dated Aug. 4, 2010 pertaining to U.S. Appl. No. 12/435,574 which is incorporated by reference in this application.

Response to Office Action for U.S. Appl. No. 12/787,796, filed Jul. 14, 2011, 11 pgs.

Notice of Allowance for U.S. Appl. No. 12/787,796 dated Oct. 18, 2011, 10 pgs.

Final Office Action for U.S. Appl. No. 12/435,574 mailed Feb. 17, 2011, 8 pgs.

Response to Final Office Action for U.S. Appl. No. 12/435,574, filed May 13, 2011, 11 pgs.

Examiner Interview Summary for U.S. Appl. No. 12/435,574 dated Jun. 10, 2011, 3 pgs.

Notice of Appeal for U.S. Appl. No. 12/435,574, filed Aug. 17, 2011, 1 pg.

Office Action for U.S. Appl. No. 12/435,574 mailed Aug. 22, 2011, 9 pgs.

Response to Office Action for U.S. Appl. No. 12/435,574, filed Nov. 22, 2011, 10 pgs.

Office Action for U.S. Appl. No. 12/435,574 mailed Mar. 30, 2012, 9 pgs.

Response to Office Action for U.S. Appl. No. 12/435,574, filed Aug. 30, 2012, 11 pgs.

International Search Report mailed Apr. 14, 2010 for PCT/US2009/067076, 8 pgs.

Hoshino, "Transendoscopic Projectile Drug Delivery", Gastroenterologia Japonica, vol. 25, No. 5, Jun. 15, 1990, 1 page.

Park et al., "A randomized comparison of a new flexible bipolar hemostasis forceps designed principally for NOTES versus a conventional surgical laparoscopic bipolar forceps for intra-abdominal vessel sealing in a porcine model", Gastrointestinal Endoscopy 2010, vol. 71, No. 4, pp. 835-841.

Fritscher-Ravens et al., "Beyond NOTES: randomized controlled study of different methods of flexible endoscopic hemostasis of artificially induced hemorrhage, via NOTES access to the peritoneal cavity", Endoscopy 2009, vol. 41, pp. 29-35.

* cited by examiner

APPARATUS AND METHODS FOR CONTAINING AND DELIVERING THERAPEUTIC AGENTS

CROSS-REFERENCE TO RELATED APPLICATIONS

This application claims the benefit of U.S. Provisional Application No. 61/140,379 filed on Dec. 23, 2008, entitled "APPARATUS AND METHODS FOR CONTAINING AND DELIVERING THERAPEUTIC AGENTS," the entire contents of which are incorporated herein by reference.

BACKGROUND

The present embodiments relate generally to medical devices, and more particularly to apparatus and methods for delivering therapeutic agents to a target site.

There are several instances in which it may become desirable to introduce therapeutic agents into the human or animal body. For example, therapeutic drugs or bioactive materials may be introduced to achieve a biological effect. The biological effect may include an array of targeted results, such as inducing hemostasis, sealing perforations, reducing restenosis likelihood, or treating cancerous tumors or other diseases.

Many of such therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites. For example, localized delivery of therapeutic agents to a tumor may reduce the exposure of the therapeutic agents to normal, healthy tissues, which may reduce potentially harmful side effects.

Localized delivery of therapeutic agents has been performed using catheters and similar introducer devices. By way of example, a catheter may be advanced towards a target site within the patient, and then the therapeutic agent may be injected through a lumen of the catheter to the target site. Typically, a syringe or similar device may be used to inject the therapeutic agent into the lumen of the catheter. However, such a delivery technique may result in a relatively weak stream of the injected therapeutic agent.

Moreover, it may be difficult or impossible to deliver therapeutic agents in a targeted manner in certain forms, such as a powder form, to a desired site. For example, if a therapeutic powder is held within a syringe or other container, it may not be easily delivered through a catheter to a target site in a localized manner that may also reduce potentially harmful side effects.

SUMMARY

The present embodiments provide apparatus and methods suitable for containing a therapeutic agent and delivering it to a target site. The apparatus generally comprises at least one container for holding a therapeutic agent, and a pressure source for facilitating delivery of the therapeutic agent.

In one embodiment, the pressure source may be placed in selective fluid communication with a proximal end of the container. Fluid from the pressure source may flow through at least a portion of the container to urge the therapeutic agent through a distal end of the container and towards the target site. The pressure source may comprise a compressed gas dispenser.

At least one tube member, such as a catheter, may be used to facilitate delivery of the therapeutic agent from the container to the target site. The catheter may be placed in fluid communication with the distal region of the container. In use, fluid from the pressure source urges the therapeutic agent through the container, through the catheter, and then distally towards the target site.

The container has a proximal end and a distal end that may be closed by pregnable sealing members. The container is designed to control the flow of therapeutic agent through the tube member in order to provide a consistent, uniform amount with each use. In one embodiment, the container comprises a tube member held preferably at about the radial center of the container near the distal end. A plug holds the tube member in place and has an outer diameter that is approximately equal to the interior of the container, so that it prevents any therapeutic agent that does not pass through the tube member from exiting the distal end of the container.

In one embodiment, a flow obstruction member is placed preferably at about the radial center of the container and proximally adjacent to the tube member. A support member, comprised of a wire or other suitable material, is coupled to the flow obstruction member and is held in place by a support structure. The support structure and support member, in combination, maintain the flow obstruction member in place. When fluid from the pressure source enters the container, it forces therapeutic agent to travel around the flow obstruction member so that a certain amount of therapeutic agent is directed through the tube member to be delivered to the target site.

In another embodiment, the container does not contain a tube member, but instead comprises flow obstruction members placed along the interior of the container that are designed to promote the delivery of a consistent, uniform amount of therapeutic agent with each use.

In any of the embodiments, switches may be placed at the proximal and distal ends of the container in order to control when fluid from the pressure source may enter the container and push the therapeutic agent into the catheter. If pregnable seals are used, the switches may also be used to perforate the seals surrounding the container. Additionally, a valve may be placed in fluid communication between the pressure source and the container so that the fluid from the pressure source bypasses the container entirely and then enters the catheter in order to clear the catheter of any excess therapeutic agent.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 8 is a schematic view of a therapeutic agent being forced past a flow obstruction member and into a tube member.

FIG. 9 is a schematic view of therapeutic agent being forced past an alternative flow obstruction member and into the tube member.

FIG. 10 is a flow chart view depicting components of an exemplary system for containing and delivering a therapeutic agent to a target site in a patient.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
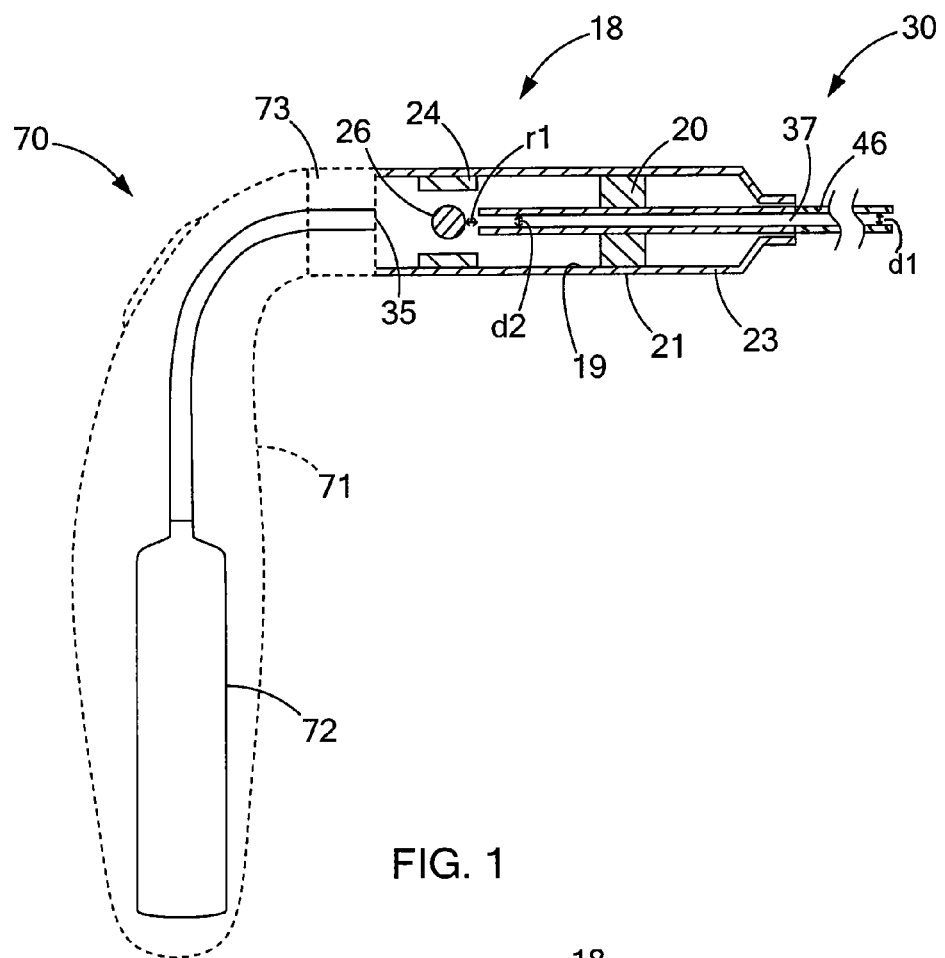
FIG. 1 is a side sectional view of an apparatus for containing and delivering therapeutic agent to a target site in a patient.

Referring now to FIG. 1, a first embodiment of an apparatus suitable for containing and delivering a therapeutic agent to a target site within a patient is shown. The apparatus comprises a pressure source 70 and a container 18 and a catheter 46. For example, as shown in FIG. 1, the pressure source 70 comprises a pressurized fluid cartridge 72, and a housing 71 that at least partially encapsulates or covers the pressurized fluid cartridge 72.

The pressure source 70 may comprise one or more components capable of producing or furnishing a fluid having a desired pressure. In one embodiment, the pressure source 70 may comprise a pressurized fluid cartridge 72 comprised of a selected gas or liquid—or a combination of gas and liquid—such as carbon dioxide, nitrogen, or any other suitable gas or liquid that may be compatible with the human body. The pressurized fluid cartridge 72 may contain the gas or liquid at a relatively high, first predetermined pressure, for example, around 1,800 psi inside of the cartridge. The fluid may flow from the pressurized fluid cartridge 72 through a pressure regulator, such as regulator valve 73 having a pressure outlet, which may reduce the pressure to a lower, second predetermined pressure or to achieve a set flow rate. Solely by way of example, the second predetermined pressure may be in the range of about 30 to about 80 psi, although any suitable pressure may be provided for the purposes described below. Therapeutic agent is disposed within the container 18. The pressure source 70 propels fluid from the pressurized fluid cartridge 72 distally through the container 18 and through the catheter 46. In other embodiments, the pressure source 70 may comprise a compressible ball or a syringe. An inner diameter d1 of the catheter 46 may vary, but a preferred inner diameter ranges from about 0.085 inches to about 0.100 inches.

Referring now to FIGS. 1-5, further features of the container 18 are described in greater detail. In this embodiment, the apparatus comprises a container 18 that that has an outer surface area 21 that is generally cylindrical, and has a preferred outer diameter ranging from about 0.90 inches to about 1.10 inches. The container 18 further comprises an interior surface 19 and a thickness 23, wherein a preferred thickness is about 0.10 inches to about 0.30 inches. The container 18 is configured to hold a therapeutic agent 33. The container 18 further comprises a support structure 24 that is preferably near a proximal end 32 of the container 18, but that could be disposed at almost any position in the container 18. The support structure 24 is connected to a flow obstruction member 26 via a support member 28. The flow obstruction member 26 is preferably positioned at about the radial center of the container 18. The support structure 24 preferably projects inwardly towards the radial center of the container 18. In this embodiment, the flow obstruction member 26 is generally spherical and the support structure 24 is generally cylindrical, preferably the support structure 24 is a ring or short-cylinder sized to fit inside the interior surface 19 of container 18. A diameter of the flow obstruction member 26 may vary, but a preferred range is about 0.25 inches to about 0.35 inches. The support member 28 may comprise a wire, rod, or other suitable materials for holding the flow obstruction member 26 in place. The support structure 24, flow obstruction member 26, and support member 28 also may be composed of one solid piece.

Figure 2:
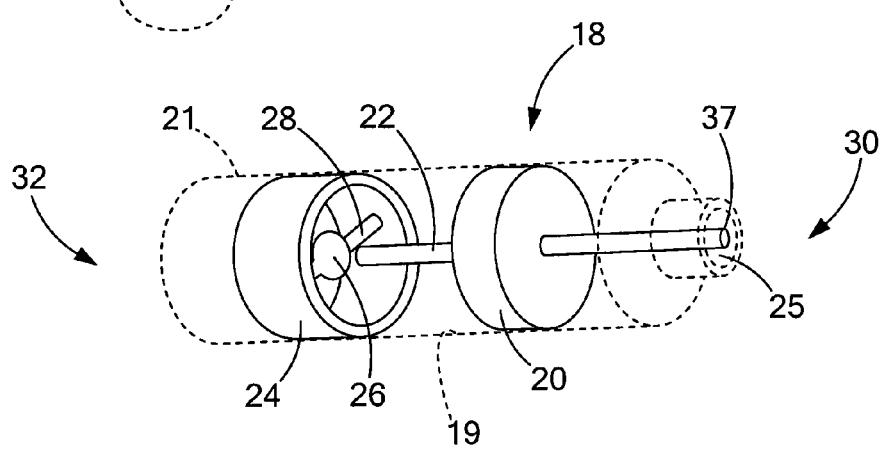
FIG. 2 is a schematic view of a first embodiment of a container.
Figure 3:
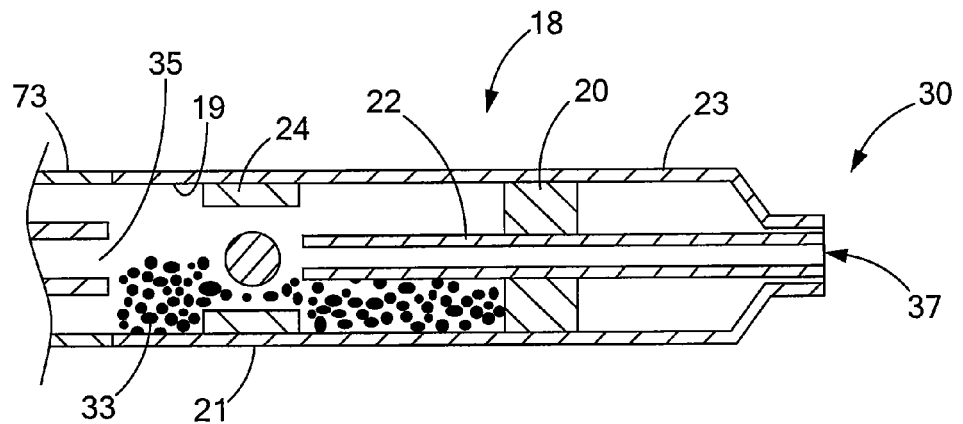
FIG. 3 is a side sectional view illustrating the first embodiment of FIG. 2 with a therapeutic agent present inside the container.
Figure 4:
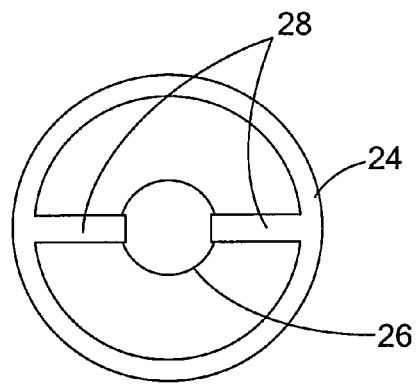
FIG. 4 is an end view of a flow obstruction member, and a support structure and support member of the embodiment of FIG. 2.
Figure 5:
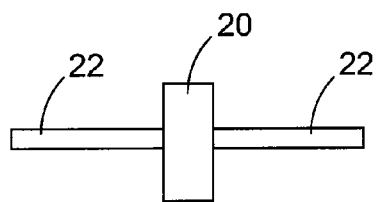
FIG. 5 is a side view of the tube member and the plug of the embodiment of FIG. 2.

The container 18 further comprises a tube member 22 that has a distal end 37 that is located near a distal end 30 of the container 18. A diameter of the tube member 22 may vary, but a preferred range in outer diameter is about 0.23 inches to about 0.27 inches and a preferred inner diameter d2 ranges from about 0.19 to about 0.22 inches. The tube member 22 extends to a position proximate to the flow obstruction member 26. While a distance r1 from the tube member 22 to the flow obstruction member 26 may vary, a preferred range of distance r1 is about 0.25 mm to about 0.35 mm. The distal end 37 of the tube member 22 may extend distally up to or beyond the distal end of the container 18. The tube member 22 preferably does not directly abut or touch the flow obstruction member 26, and is held preferably at about the radial center of the container 18 by a plug 20. In this embodiment, the plug 20 is disc-shaped. An outer diameter of the plug 20 is equal to or slightly less than a diameter of an interior surface 19 of the container 18 so as to form a seal between the plug 20 and the interior surface 19 to prevent any therapeutic agent from reaching the distal end 30 of the container 18 without passing through the tube member 22. The container 18 may also be sealed by sealing members 25, with one at the distal end 30 as depicted in FIG. 2 and another sealing member 25 located at the proximal end 32 (not shown). In alternative embodiments where the distal end 37 of the tube member 22 extends distally past the distal end 30 of the container 18, the sealing member 25 would encapsulate the distal end 37 of the tube member 22.

The container 18 may comprise any suitable size and shape for holding a therapeutic agent 33. In alternative embodiments wherein the container is not cylindrical in shape, the support structure 24 and the plug 20 will be made out of shapes necessary to prevent therapeutic agent from reaching the distal end 30 through routes other than through the tube member 22.

Figures 8, 9, 10:
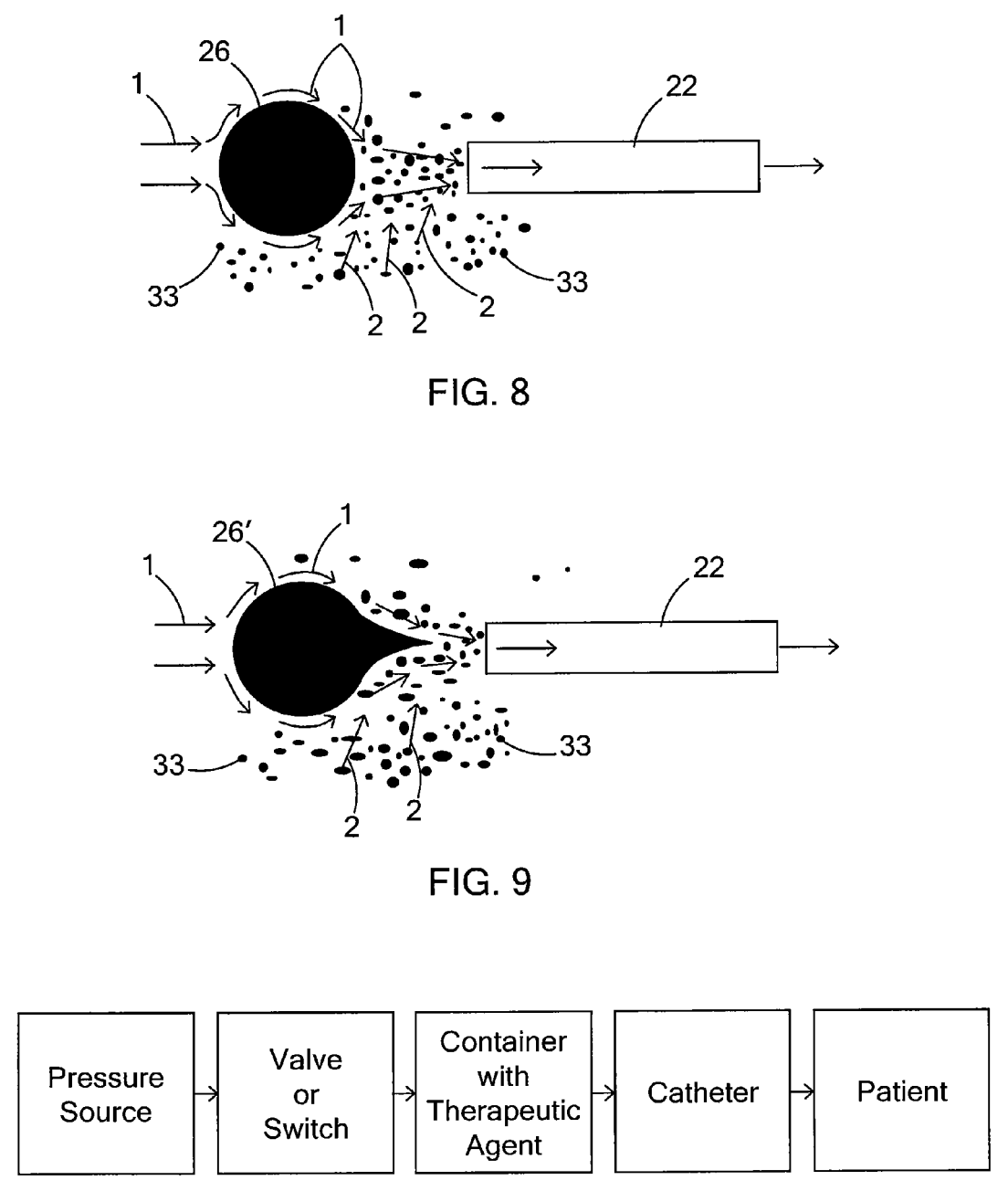

The flow obstruction member 26 may comprise any suitable shape for controlling the rate of flow of the therapeutic agent into the tube member 22. When fluid from the pressure source 70 enters the container 18 through an inlet port 35, the fluid travels around the flow obstruction member 26 and tends to travel along the surface of the flow obstruction member 26. As the fluid continues past the tube member 22, the fluid creates a pressure differential wherein the resulting lower pressure within the tube member 22 draws therapeutic agent 33 into the tube member 22. Without the flow obstruction member 26, the therapeutic agent 33 would flow in a haphazard, turbulent manner toward the distal end of the container 18, and a non-uniform amount of therapeutic agent 33 would pass through the tube member 22. As depicted in FIGS. 8 and 9, the flow obstruction members produce a more laminar flow of therapeutic agent 33, and therefore, a uniform amount of therapeutic agent 33 passes through the tube member 22. Arrows labeled 1 indicate the flow of the fluid around the flow obstruction member 26, and arrows labeled 2 represent the therapeutic agent 33 being drawn into the tube member 22. The more laminar flow caused by the flow obstruction member 26 may result in a generally uniform dispersion of the therapeutic agent 33 and the fluid within the tube member 22. A preferred ratio of fluid to therapeutic agent 33 may range from about 1:5 to about 1:1, but is most preferably about 1:1. The more laminar flow caused by the flow obstruction member 26 may also result in a consistent volumetric flow rate, which is a range of about +/−10% of a predetermined flow rate. The uniformity and consistency of the mixture and its flow may vary depending on the fluid and agent used (e.g., based on particle size, density, viscosity, etc.) as will readily be appreciated by those skilled in the art.

Depicted in FIGS. 8 and 9 are a sphere-shaped flow obstruction member 26 and a tear drop-shaped flow obstruction member 26', respectively. Referring to FIG. 9, the tip of the "tear" extends longitudinally toward the tube member 22. In another embodiment, the flow obstruction member 26 may comprise a dimpled sphere shape, similar to a golf ball. The tear drop-shaped flow obstruction member 26' of FIG. 9 may result in a more laminar flow than the sphere-shaped flow obstruction member 26 of FIG. 8 and is preferred.

The container 18 also may comprise measurement indicia, which allow a user to determine a quantity of the therapeutic agent 33 that is held within the container 18, as explained in commonly assigned pending U.S. application Ser. No. 12/435,574 ("the '574 application"), filed May 5, 2009, which is hereby incorporated by reference in its entirety. Optionally, a valve member may be disposed between the reservoir of the container 18 and the catheter 46 to selectively permit and inhibit fluid communication between the container 18 and the catheter 46, as further described in the '574 application.

Referring now to FIGS. 1 and 10-12, an actuator, such as a button, may be used to selectively actuate the pressure source 70. The pressurized fluid may flow from the pressurized fluid cartridge 72, and subsequently through the regulator valve 73 using an adapter, as explained in the '574 application. The adapter may be configured to be sealingly coupled to the pressurized fluid cartridge 72, as further explained in the '574 application. Further, the adapter may be coupled to tubing, which allows the pressurized fluid to flow into the regulator valve. A proximal end of a different tubing may be adapted to be coupled to the regulator valve 73, as shown in the '574 application, thereby enabling the pressurized fluid to flow through the regulator valve 73 and into the tubing at the lower, second predetermined pressure.

The pressure source 70 optionally may comprise one or more commercially available components. Solely by way of example, the pressurized fluid cartridge 72 may comprise a disposable carbon dioxide cartridge, such as the Visage® commercial dispenser manufactured by Helen of Troy®, El Paso, Tex. The pressure source 70 therefore may comprise original or retrofitted components capable of providing a fluid or gas into the tubing at a desired regulated pressure.

Figure 11:
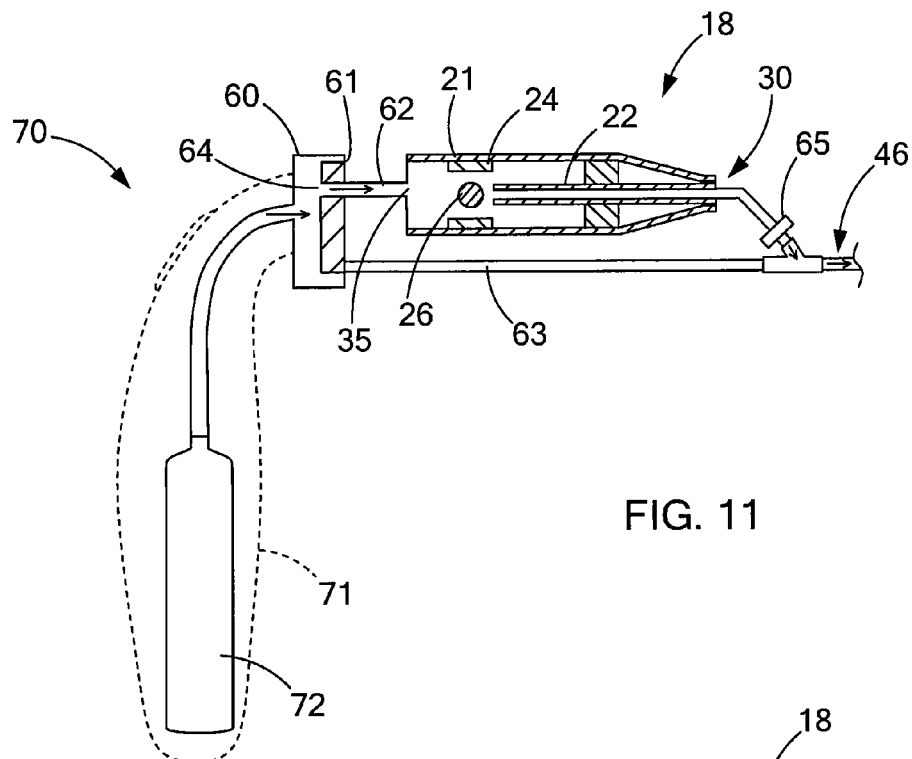
FIG. 11 is a schematic view of an apparatus for containing and delivering a therapeutic agent to a target site in a patient in accordance with one embodiment.
Figure 12:
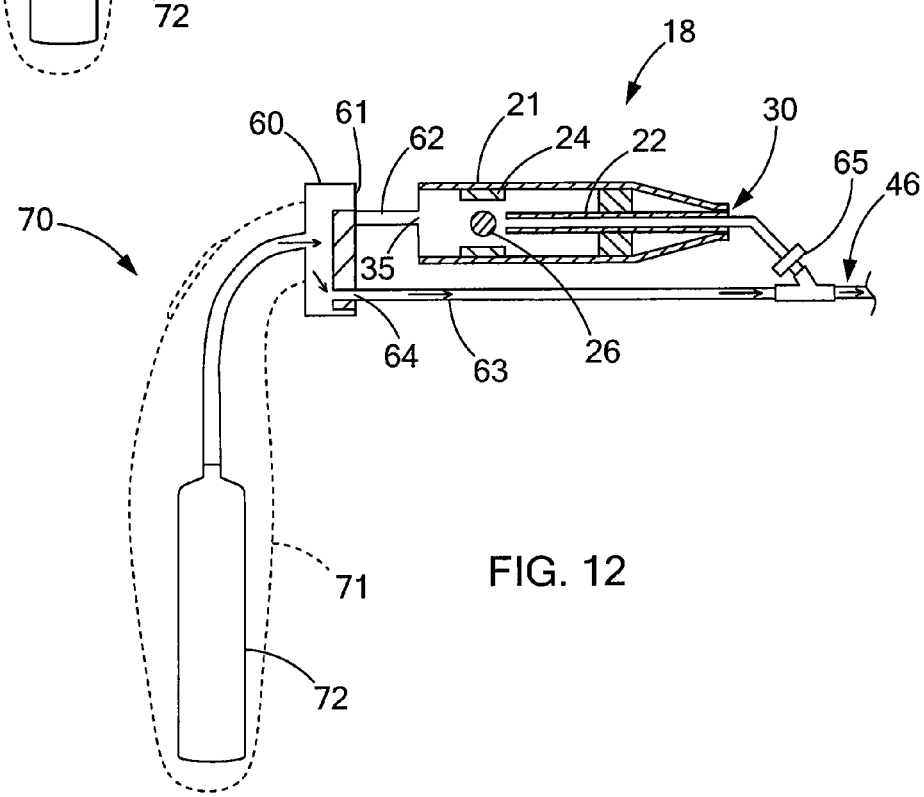
FIG. 12 is a schematic view of an apparatus for clearing a therapeutic agent out of a catheter.

One or more catheters may be used to deliver the therapeutic agent 33 to a target site. Referring to FIGS. 1, 11, and 12, the catheter 46 comprises a proximal end that may be placed in fluid communication with the distal end 30 of the container 18 using a suitable coupling mechanism or arrangement. The catheter 46 further comprises a distal end that may facilitate delivery of the therapeutic agent 33 to a target site, as set forth below. The catheter 46 may comprise a flexible, tubular member that may be formed from one or more semi-rigid polymers. For example, the catheter may be manufactured from polyurethane, polyethylene, tetrafluoroethylene, polytetrafluoroethylene, fluorinated ethylene propylene, nylon, PEBAX or the like.

Figure 13:
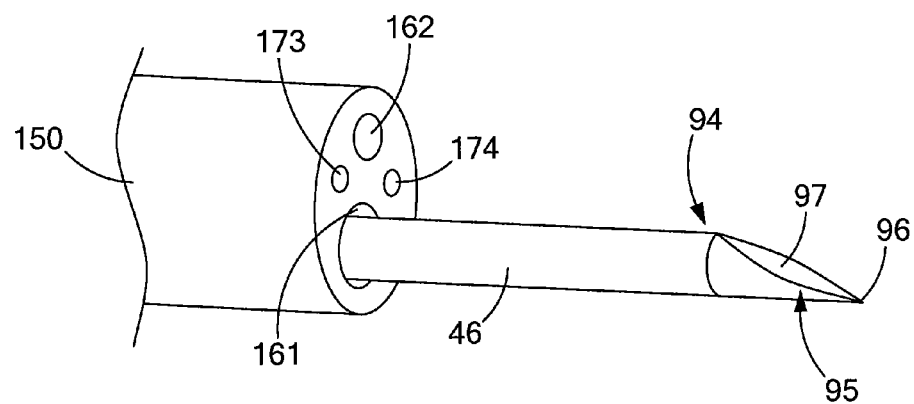
FIG. 13 is a perspective view of a distal end of an exemplary end-viewing endoscope and a needle that may be used in conjunction with the apparatus of FIG. 1.

Referring to FIG. 13, the apparatus for delivering the therapeutic agent may further comprise an endoscope 150 and a needle 95 suitable for penetrating tissue, or just a needle without the endoscope (not shown). The needle 95 may be coupled to a distal end 94 of the catheter 46 to form a sharp, distal region configured to pierce through a portion of a patient's tissue, or through a lumen wall to perform a translumenal procedure. In FIG. 13, the needle 95 may be formed as an integral component with the catheter 46, i.e., such that distal movement of the catheter 46 causes distal advancement of the needle 95. In this embodiment, a relatively sharp needle tip may be affixed to the distal tip of the catheter 90, e.g., using an adhesive, to form a needle-shaped element at the distal end of the catheter. Alternatively, a separate needle configured to be inserted through a lumen of the catheter 90 may be employed.

In addition, end-viewing and side-viewing endoscopes may be used, as described in the '574 application. The endoscopes may be advanced through a bodily lumen such as the alimentary canal to a position proximate the target location. The catheter 46 then may be advanced through the working lumen of the endoscope. If the needle 95 is employed, a sharpened tip 96 of the needle 95 may extend distal to the endoscope, and may be used to puncture through an organ or a gastrointestinal wall or tissue. At this time, the therapeutic agent 33 may be delivered through the catheter 46, then through a bore 97 in the needle 95, in the manner described above and in the '574 application.

In operation, the apparatus of FIGS. 1 and 10-13 may be used to deliver the therapeutic agent 33 to a target site within a patient's body. In a first step, the distal end of the catheter 46 may be positioned in relatively close proximity to the target site. The catheter 46 may be advanced to the target site using an open technique, a laparoscopic technique, an intraluminal technique, using a gastroenterology technique through the mouth, colon, or using any other suitable technique.

The catheter 46 may comprise one or more markers (not shown), which may be disposed near the distal end of the catheter 46. The markers may be configured to be visualized under fluoroscopy or other imaging techniques to facilitate location of the distal end of the catheter 46. If the needle 95 is integral to the catheter 46, the needle 95 also may be visualized using the imaging techniques, thereby allowing placement of the distal end of the catheter 46 in close proximity to the target site. If desired, the catheter 46 may be advanced through a working lumen of an endoscope, as explained in further detail in the '574 application.

When the catheter 46 is positioned at the desired location, the pressure source 70 may be actuated. As noted above, a button or other actuator may be coupled to the pressurized fluid cartridge 72 to release a relatively high pressure fluid. As noted above, the pressurized fluid may flow through a regulator valve 73 and through the container 18 at a desired pressure and rate. For example, the regulator valve may automatically set the pressure for fluid flow, or alternatively, a control mechanism coupled to the pressurized fluid cartridge and/or the regulator valve may be activated by a user to set the desired pressure for fluid flow into the container 18. Such a control mechanism also may be used to variably permit fluid flow into the container 18, e.g., fluid from the pressurized fluid cartridge 72 may flow into the container 18 at a desired time interval, for example, a predetermined quantity of fluid per second. Moreover, the control mechanism may be pre-programmed to deliver a predetermined amount of the therapeutic agent, depending on the type, viscosity, and other properties of the agent. Empirical information, such as a table of pressure, time and delivered quantity, may be stored and used for the different agents or procedures.

Fluid from the pressure source 70 flows through the proximal end 32 of the container 18, around the obstruction flow member 26 and into the tube member 22, through the distal end 30 and then through a lumen of the catheter 46. Fluid may exit the distal end of the catheter 46, for example, through a bore formed in the needle 95. In addition, the orientation of container 18 in regards to the pressure source 70 may vary. For example, the container 18 may be aligned parallel to the pressure source 70 as described in U.S. Application No. 61/182,463 filed May 29, 2009, the disclosure of which is incorporated herein by reference in its entirety.

As noted above, a valve member optionally may be disposed between the reservoir of the container 18 and a connecting member, as shown in the '574 application. A user may selectively actuate the valve member to periodically permit and inhibit fluid communication between the container and the connecting member. The valve member also may serve as a "shut-off" safety mechanism to inhibit withdrawal of the therapeutic agent from the reservoir, even when pressurized fluid is flowing through the connecting member.

As noted above and depicted in the '574 application, a control mechanism coupled to the pressure source 70 may variably permit fluid flow into the tubing from the pressurized fluid cartridge 72 at a desired time interval, for example, a predetermined quantity of fluid per second. In this manner, pressurized fluid may flow through the catheter periodically, and the therapeutic agent 33 may be delivered to a target site at a predetermined interval or otherwise periodic basis.

The apparatus may be used to deliver the therapeutic agent 33 in a wide range of procedures and the therapeutic agent 33 may be chosen to perform a desired function upon ejection from the distal end of the catheter 46. Solely by way of example, and without limitation, the provision of the therapeutic agent 33 may be used for providing hemostasis; closing perforations; performing lithotripsy; delivering drugs; treating tumors and cancers; and treating renal dialysis fistulae stenosis, vascular graft stenosis, and the like. The size of the catheter 46 used to deliver the therapeutic agent 33 may vary depending upon the procedure for which it is being used; for example, a short catheter may be used for external use on irregularly shaped lacerations. The size of the therapeutic agent 33 may also vary, although a preferred embodiment of a therapeutic agent 33 for hemostasis has a 325 mesh size.

The therapeutic agent 33 can be delivered during procedures such as coronary artery angioplasty, renal artery angioplasty and carotid artery surgery, or may be used generally for treating various other cardiovascular, respiratory, gastroenterology or other conditions. The above-mentioned systems also may be used in transvaginal, umbilical, nasal, and bronchial/lung related applications.

For example, if used for purposes of hemostasis, thrombin, epinephrine, or a sclerosant may be provided to reduce localized bleeding. Similarly, if used for closing a perforation, a fibrin sealant may be delivered to a localized lesion. In addition to the hemostatic properties of the therapeutic agent 33, it should be noted that the relatively high pressure of the fluid and therapeutic agent, by itself, may act as a mechanical tamponade by providing a compressive force, thereby reducing the time needed to achieve hemostasis.

The therapeutic agent 33 may be selected to perform one or more desired biological functions, for example, promoting the ingrowth of tissue from the interior wall of a body vessel, or alternatively, to mitigate or prevent undesired conditions in the vessel wall, such as restenosis. Many other types of therapeutic agents 33 may be used in conjunction with the apparatus.

The therapeutic agent 33 may be delivered in any suitable form. For example, the therapeutic agent 33 may comprise a powder, liquid, gel, aerosol, or other substance. Advantageously, the pressure source 70 may facilitate delivery of the therapeutic agent 33 in any one of these forms.

The therapeutic agent 33 employed also may comprise an antithrombogenic bioactive agent, e.g., any bioactive agent that inhibits or prevents thrombus formation within a body vessel. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; anti-platelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Additionally, or alternatively, the therapeutic agent 33 may include thrombolytic agents used to dissolve blood clots that may adversely affect blood flow in body vessels. A thrombolytic agent is any therapeutic agent that either digests fibrin fibers directly or activates the natural mechanisms for doing so. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA. While a few exemplary therapeutic agents 33 have been listed, it will be apparent that numerous other suitable therapeutic agents may be used in conjunction with the apparatus and delivered through the catheter 46.

Advantageously, the apparatus permits localized delivery of a desired quantity of the therapeutic agent 33 at a desired pressure via the pressure source 70. Since the distal end of the catheter 46 may be placed in relatively close proximity to a target site, the apparatus provides significant advantages over therapeutic agents delivered orally or through an IV system and may reduce accumulation of the therapeutic agent 33 in healthy tissues, thereby reducing side effects. Moreover, the delivery of the therapeutic agent 33 to the target site is performed in a relatively fast manner due to the relatively high pressure of the fluid, thereby providing a prompt delivery to the target site compared to previous devices.

Further, if the optional needle 95 is employed, the apparatus advantageously may be used both to perforate tissue at or near a target site, and then deliver the therapeutic agent 33 at a desired pressure in the manner described above. For example, the needle 95 may comprise an endoscopic ultrasound (EUS) needle. Accordingly, in one exemplary technique, a sharpened tip of the needle 95 may be capable of puncturing through an organ or a gastrointestinal wall or tissue, so that the therapeutic agent 33 may be delivered at a predetermined pressure in various bodily locations that may be otherwise difficult to access. One or more delivery vehicles, such as an endoscope or sheath, may be employed to deliver the catheter 46 to a target site, particularly if the distal end of the catheter 46 comprises the optional needle 95.

Figure 6:
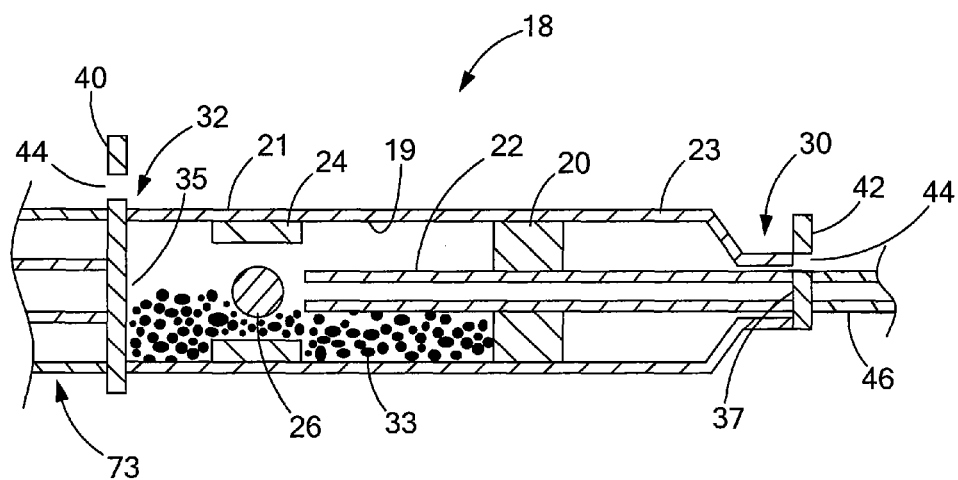
FIG. 6 is a side sectional view of the embodiment of FIG. 2 with switches depicted in a closed state.
Figure 7:
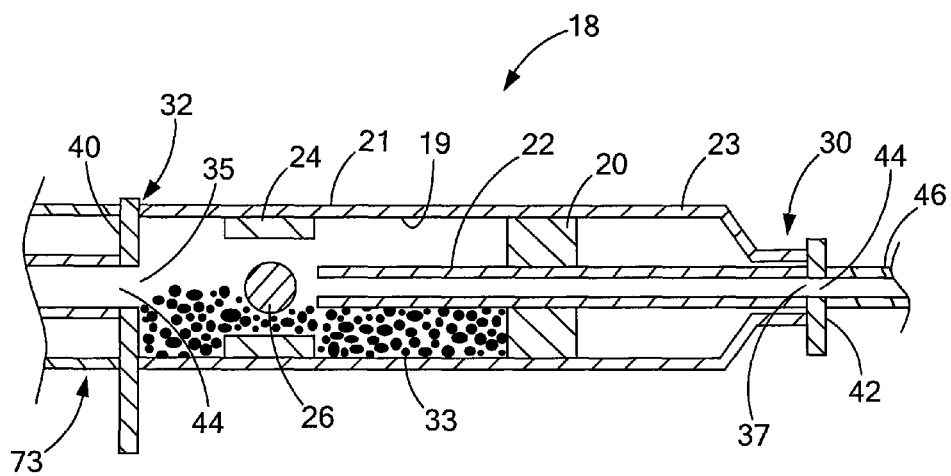
FIG. 7 is a side sectional view of the embodiment of FIG. 2 with switches depicted in an open state.

Referring now to FIGS. 6 and 7, in this embodiment, a switch 40 may be used to selectively open and close the proximal end 32 of the container 18, and a switch 42 may be used to selectively open and close the distal end 37 of the tube member 22. Each of the switches 40 and 42 contain an opening 44 therein. When the switches 40 and 42 are depressed into the open position as depicted in FIG. 7, fluid from the pressure source 70 will enter the proximal end 32 of the container 18 and will propel at least some therapeutic agent 33 within the container 18 through the tube member 46 to be delivered to a target site. In the closed position depicted in FIG. 6, no fluid from the pressure source 70 will be able to enter the container 18, and therefore no therapeutic agent will be delivered to the target site.

In the embodiment depicted in FIGS. 6 and 7, the switches 40 and 42 may be used with or without the sealing members 25. When the switches 40 and 42 are used in conjunction with the sealing members 25, they perforate the sealing members 25 when depressed into the open position for the first time, thereby allowing at least some therapeutic agent 33 to travel through the distal end 37 of the tube member 22 and into the catheter 46 to be delivered to a target site. When returned to the closed position depicted in FIG. 6, the switches 40 and 42 prevent therapeutic agent from entering the catheter 46 even after the sealing members 25 have been perforated. In an alternative embodiment, stopcocks or valves that are typically used with catheters could substitute for the switches 40 and 42. In yet another embodiment, threaded luers with male and female ends could be used wherein the distal end 37 of the tube member 22 is the male end of a threaded luer.

Referring again to FIGS. 11 and 12, a clearing valve 60 may be used. In the "on" position, a piston 61 having an opening 64 formed therein is located in the valve 60 so that the opening 64 is in fluid communication with a proximal end of a first hollow tube 62, such as a catheter. A distal end of the hollow tube 62 is in fluid communication with a container holding therapeutic agent 33. In this embodiment, fluid from the pressure source 70 travels through the valve 60 and the hollow tube 62 and into the container 18, where it can propel therapeutic agent 33 through the distal end 30 of the container 18 and deliver the therapeutic agent 33 through the catheter 46 to a target site within a patient. In the "off" position depicted in FIG. 12, the piston 61 is located so that the opening 64 is aligned with a second hollow tube 63 that is not in fluid communication with the container 18. In this embodiment, fluid from the pressure source 70 passes through the catheter 46 and forces any therapeutic agent 33 that may have accumulated in the catheter 46 to exit the catheter 46. A check valve 65, or a one-way valve—located at a position distal to the container and proximal to the catheter 46—prevents any therapeutic agent 33 from traveling into the catheter 46. This ensures that when the valve 60 is in the "on" position, a uniform amount of therapeutic agent 33 is delivered to a target site within a patient.

Figure 14:
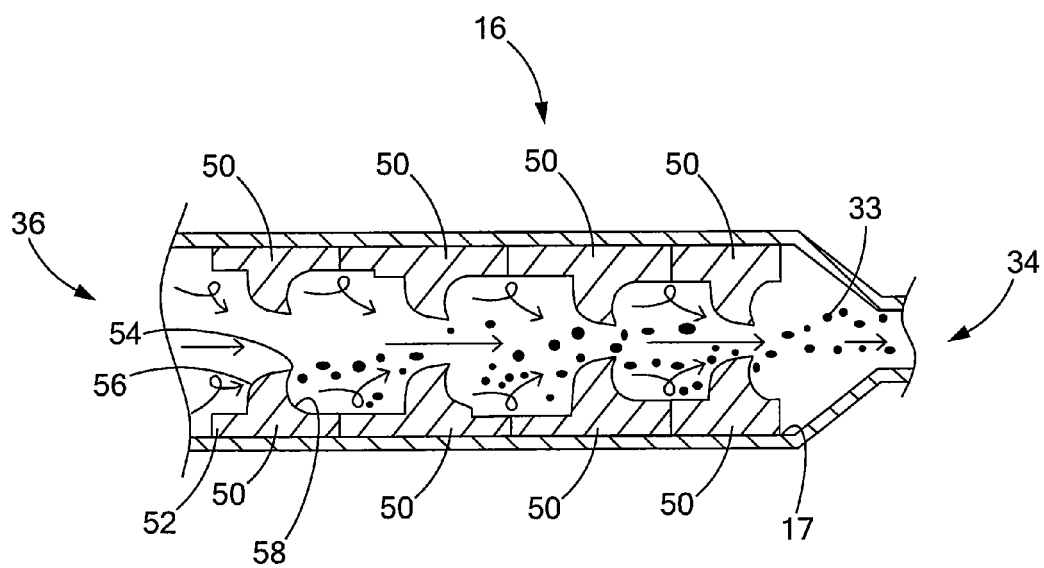
FIG. 14 is a side sectional view of an alternative embodiment of a container.

Referring now to FIG. 14, an alternative embodiment for containing therapeutic agent 33 and delivering a uniform amount of therapeutic agent 33 is shown. Instead of one flow obstruction member and a tube member of the embodiment shown in FIG. 1, the embodiment of FIG. 14 comprises multiple flow obstruction members 50 aligned along an interior surface 17 of a container 16. Each flow obstruction member 50 has a preferred annular shape comprising a base 52 secured to the interior surface 17 of the container 16, a peak 54, a convex proximal side 56, and a concave distal side 58, although the proximal side 56 and the distal side 58 may also be concave and convex, respectively.

In the embodiment of FIG. 14, when the fluid from a single blast of the pressure source 70 enters the container 16 through the proximal end 36, a relatively uniform amount of the therapeutic agent 33 contained within the container 16 is propelled longitudinally through the container 16 and out through the distal end 34. The relatively uniform amount is obtained, because some therapeutic agent 33 becomes obstructed by and accumulates behind and around the flow obstruction members 50 after the fluid from the pressure source enters and moves toward the distal end 34 of the container 16. During each blast, a certain amount of therapeutic agent 33 that has accumulated behind each flow obstruction member 50 is picked up by the longitudinally advancing fluid and is circulated towards the distal end 34 of the container 16. In FIG. 14, the flow obstruction members 50 are depicted as being peak-shaped, but they may comprise any shape suitable for obstructing or halting the flow of some of the therapeutic agent 33 in order to assure that a relatively uniform amount of therapeutic agent 33 is allowed out of the container 16 per blast from the pressure source 70.

Figure 15:
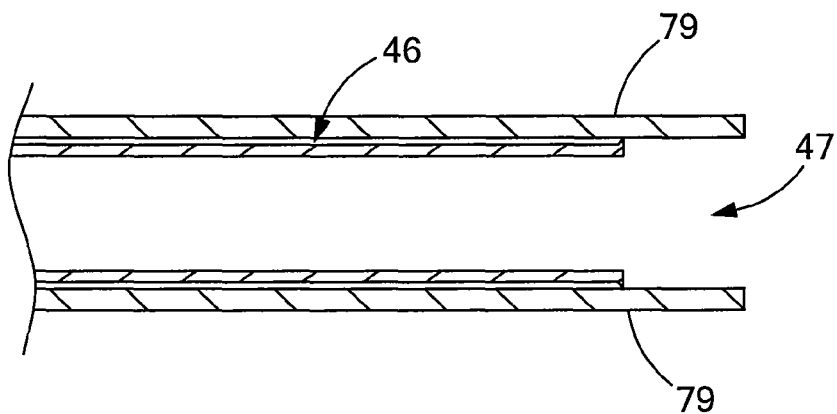
FIG. 15 is a side sectional view of one embodiment of a catheter in a delivery state.
Figure 16:
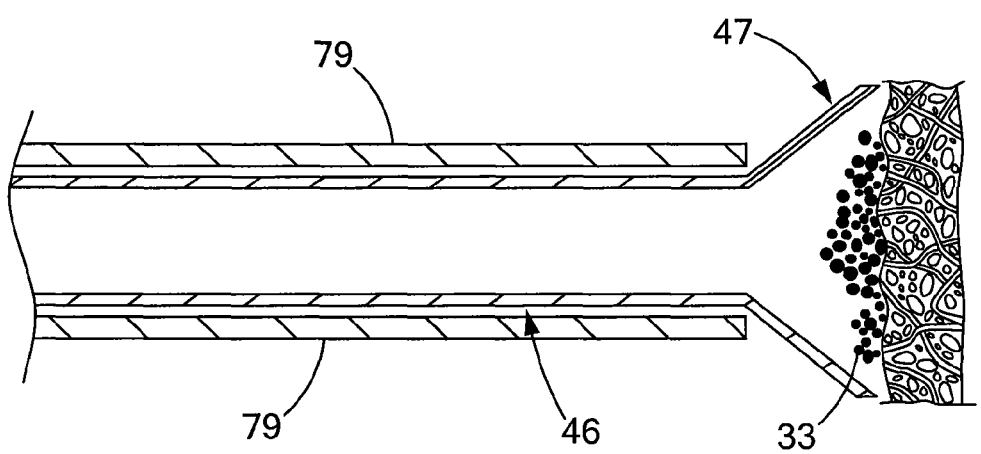
FIG. 16 is a side sectional view of one embodiment of a catheter in a deployed state.

Referring now to FIGS. 15 and 16, an alternative embodiment of the catheter 46 is shown, which may be substituted for any embodiments of the catheter 46 previously described herein. In this embodiment, the catheter 46 is comprised of a shape-memory material and is enclosed within an outer sheath 79. When covered by the sheath 79, the catheter 46 remains in the delivery state as depicted in FIG. 15. When the outer sheath 79 is retracted, a distal end 47 of the catheter 46 expands in a radial direction in the deployed state as depicted in FIG. 16. The distal end 47 of the catheter 46 may comprise nitinol or any other suitable shape-memory material such as those described in U.S. application Ser. No. 12/428,226 filed Apr. 22, 2009, the disclosure of which is incorporated herein by reference in its entirety. The distal end 47 may be coated with a fabric or lubricious polymer such as ethylene tetrafluoroethylene ("ETFE"). When used in conjunction with an endoscope 150, the sheath 79 and the catheter 46 within may pass through the lumen 161 of the endoscope 150. The catheter 46 of this embodiment may allow for the therapeutic agent to be delivered in a more precise manner to the target site. By using the sheath 79 to maintain the catheter 46 and the distal end 47 in the delivery state, other items may be passed through the endoscope 150 or lumen 161 simultaneously with the catheter 46.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. Apparatus suitable for facilitating delivery of a therapeutic agent, the apparatus comprising:
    a pressure source;
    a container having proximal and distal ends with an inlet port at the proximal end for receiving a fluid from the pressure source;
    a therapeutic agent disposed within the container;
    a tube member having proximal and distal ends, the proximal end of the tube member positioned within the container; and
    a flow obstruction member positioned within the container between the inlet port and the proximal end of the tube member, the flow obstruction member structured to direct fluid around the flow obstruction member and towards the proximal end of the tube member, the flow obstruction member and the tube member being spaced relative to each other to cause the fluid to flow around the obstruction member and draw the therapeutic agent into the tube member and direct the therapeutic agent distally therethrough.

2. The apparatus of claim 1 further comprising at least one sealing member located at the proximal end and at least one sealing member located at the distal end of the container.

3. The apparatus of claim 1 further comprising:
    a switch located at the proximal end and a switch located at the distal end of the container;
    an opening located in the interior of each switch;
    the switches having a first position wherein the openings are not in fluid communication with the proximal and distal ends of the container; and
    the switches having a second position wherein the switches are in fluid communication the proximal and distal ends of the container.

4. The apparatus of claim 1 wherein the flow obstruction member comprises a sphere shape.

5. The apparatus of claim 1 wherein the flow obstruction member comprises a tear drop shape oriented with the rounded end facing the inlet port.

6. The apparatus of claim 1 further comprising a support structure connected to the container and having a support member projecting radially inwardly and connected to the flow obstruction member via a support member.

7. The apparatus of claim 6 wherein a plug maintains the tube member in about the radial center of the container.

8. The apparatus of claim 1 wherein the container has an outer diameter ranging from about 0.90 inches to about 1.10 inches, the flow obstruction member has a diameter ranging from about 0.25 inches to about 0.35 inches, the tube member has an inner diameter ranging from about 0.19 to about 0.22 inches, and a distance between the flow obstruction member and the tube member ranging from about 0.25 mm to about 0.35 mm.

9. The apparatus of claim 1 wherein the fluid and the therapeutic agent are mixed together within the tube member to form a mixture, the mixture having a generally uniform dispersion of the therapeutic agent within the fluid.

10. The apparatus of claim 1 wherein the fluid and the therapeutic agent are mixed together within the tube member to form a mixture, the mixture having a consistent volumetric flow rate of therapeutic agent.

* * * * *